(12) United States Patent
Kanehira et al.

(10) Patent No.: US 8,992,958 B2
(45) Date of Patent: Mar. 31, 2015

(54) ULTRASONIC CANCER TREATMENT ENHANCER AND CELL KILLER

(75) Inventors: Koki Kanehira, Kitakyushu (JP); Shuji Sonezaki, Kitakyushu (JP); Yumi Ogami, Yukuhashi (JP); Toshiaki Banzai, Kitakyushu (JP)

(73) Assignee: Toto Ltd., Fukuoka-ken (JP)

( * ) Notice: Subject to any disclaimer, the term of this patent is extended or adjusted under 35 U.S.C. 154(b) by 1569 days.

(21) Appl. No.: 11/883,208

(22) PCT Filed: Oct. 26, 2006

(86) PCT No.: PCT/JP2006/321392
§ 371 (c)(1),
(2), (4) Date: Jun. 6, 2008

(87) PCT Pub. No.: WO2007/049708
PCT Pub. Date: May 3, 2007

(65) Prior Publication Data
US 2008/0262349 A1 Oct. 23, 2008

(30) Foreign Application Priority Data

Oct. 26, 2005 (JP) .................... 2005-311871
Mar. 24, 2006 (JP) .................... 2006-83757
Jun. 21, 2006 (JP) .................... 2006-171843
Sep. 12, 2006 (JP) .................... 2006-246757

(51) Int. Cl.
| | | |
|---|---|---|
| A61N 7/00 | (2006.01) | |
| A61K 33/30 | (2006.01) | |
| A61K 33/24 | (2006.01) | |
| A61K 41/00 | (2006.01) | |
| B82Y 5/00 | (2011.01) | |
| A61K 9/00 | (2006.01) | |
| A61K 9/19 | (2006.01) | |

(52) U.S. Cl.
CPC ............ *A61K 33/30* (2013.01); *A61K 9/0019* (2013.01); *A61K 9/19* (2013.01); *A61K 33/24* (2013.01); *A61K 41/0033* (2013.01); *B82Y 5/00* (2013.01)
USPC .............................. 424/405; 600/439; 601/2

(58) Field of Classification Search
USPC ....................................................... 424/489
See application file for complete search history.

(56) References Cited

U.S. PATENT DOCUMENTS

| | | | |
|---|---|---|---|
| 5,534,585 A * | 7/1996 | Roulstone et al. ............ | 524/497 |
| 6,599,631 B2 | 7/2003 | Kambe et al. | |
| 6,677,606 B1 | 1/2004 | Rajh et al. | |
| 2001/0031498 A1 | 10/2001 | Leclercq et al. | |
| 2001/0041163 A1 * | 11/2001 | Sugita et al. ................... | 424/9.5 |
| 2003/0143161 A1 * | 7/2003 | Kawabata et al. ............ | 424/9.52 |
| 2003/0167878 A1 | 9/2003 | Al-Salim et al. | |
| 2004/0067485 A1 * | 4/2004 | Mayes et al. ...................... | 435/5 |
| 2004/0068207 A1 | 4/2004 | Tabata | |
| 2004/0091604 A1 | 5/2004 | Dempsey et al. | |
| 2004/0120884 A1 | 6/2004 | Sherman | |
| 2006/0264520 A1 | 11/2006 | Sonezaki et al. | |

FOREIGN PATENT DOCUMENTS

| | | | |
|---|---|---|---|
| EP | 1 630 136 A1 | 3/2006 | |
| JP | 01-146829 | 6/1989 | |
| JP | 03-261467 | 11/1991 | |
| JP | 04-357941 A | 12/1992 | |
| JP | 11-255516 A | 9/1999 | |
| JP | 2000-247978 | 9/2000 | |
| JP | 2001-200050 A | 7/2001 | |
| JP | 2001-302548 | 10/2001 | |
| JP | 2002-047208 | 2/2002 | |
| JP | 2002-241307 | 8/2002 | |
| JP | 2002-316946 | 10/2002 | |
| JP | 2003-026406 | 1/2003 | |
| JP | 2003026406 A1 * | 1/2003 | ................... 424/401 |
| JP | 2003-226654 | 8/2003 | |
| JP | 2003-267914 | 9/2003 | |
| JP | 2004-051863 A | 2/2004 | |
| JP | 2004-243507 A | 9/2004 | |
| JP | 2005-007392 A | 1/2005 | |
| WO | 98/01131 A1 | 1/1998 | |
| WO | WO 2004/063200 A1 | 7/2004 | |
| WO | WO 2006/116752 A2 | 11/2006 | |

OTHER PUBLICATIONS

JP 2003-26406 translation. (JP 2003-26406 document was submitted in the IDS of Jul. 27, 2007).*
JP2003026406A1 translation. "Shigeru et al."*
Cai, Ruxiong; Kubota, Yoshinobu; Shuin, Taro; et al. "Induction of Cytotoxicity by Photoexcited TiO2 Particles" Cancer Research 1992; 52:2346-2348. Published online Apr. 1, 1992.*
Barbe et al., "Nanocrystalline Titanium Oxide Electrodes for Photovoltaic Applications", J. Am. Ceram. Soc., 80 3157-71 (1997).
XP-002465884, Databsed WPI Week 199202; Derwent Publications Ltd. London, GB.
Bakalova et al., "Quantum Dot anti-CD Conjugates: Are They Potential Photosensitizers or Potentiators of Classical Photosensitizing Agents in Photodynamic Therapy of Cancer?", *Nano Letters* v.4, n.9 (2004): pp. 1567-1573.
Bakalova et al., "Quantum dots as photosensitizers?", *Nature Biotechnology*. v.22, n.11 (Nov. 2004): p. 1360.

* cited by examiner

*Primary Examiner* — Audrea Buckley
(74) *Attorney, Agent, or Firm* — Carrier Blackman & Associates, P.C.; Joseph P. Carrier; William D. Blackman

(57) ABSTRACT

There is provided an ultrasonic cancer treatment enhancer and cell killer that can significantly improve the effect of treating cancer by ultrasonic irradiation while ensuring a high level of safety. The ultrasonic cancer treatment enhancer and cell killer comprise metal semiconductor particles and can be activated upon ultrasonic irradiation to kill or destruct cancer cells.

15 Claims, 7 Drawing Sheets

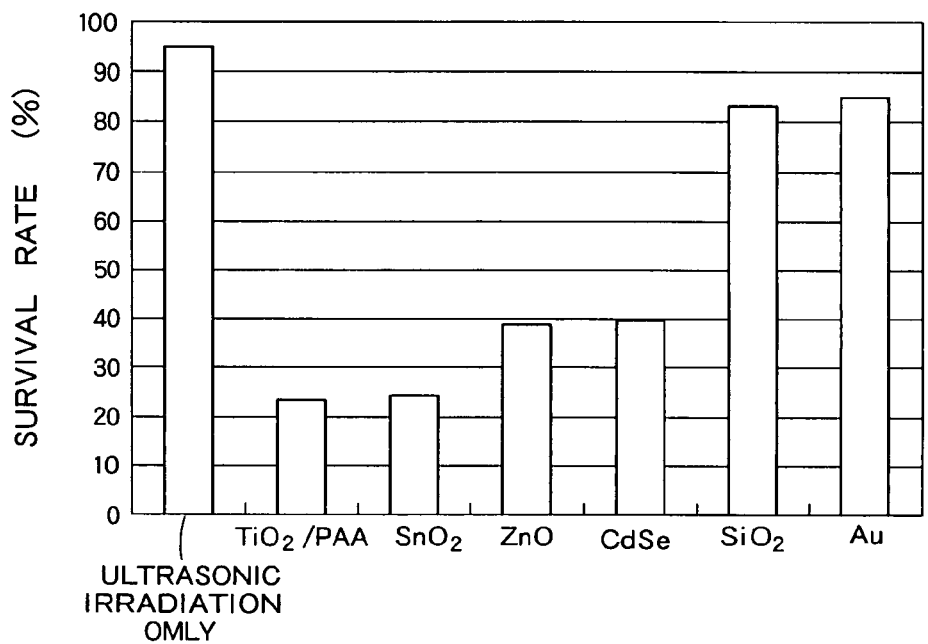
F I G. 1
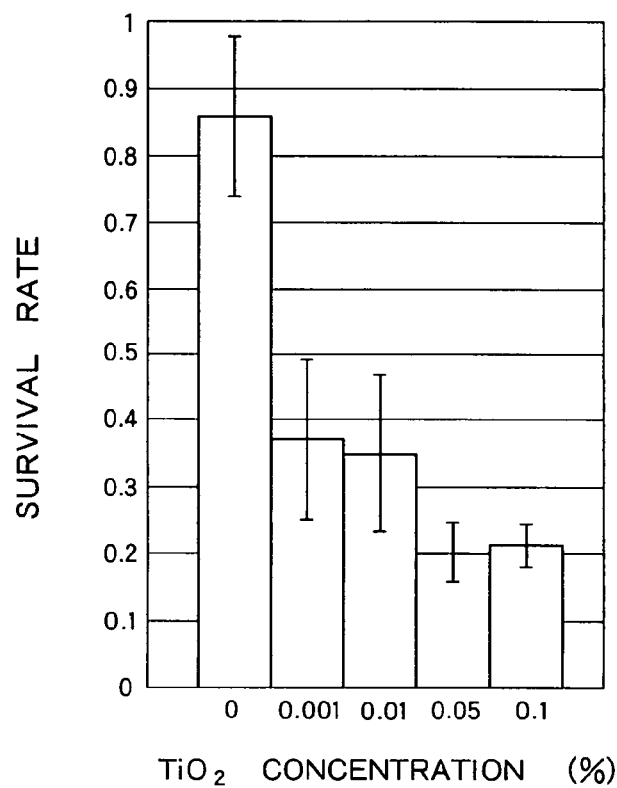
F I G. 2

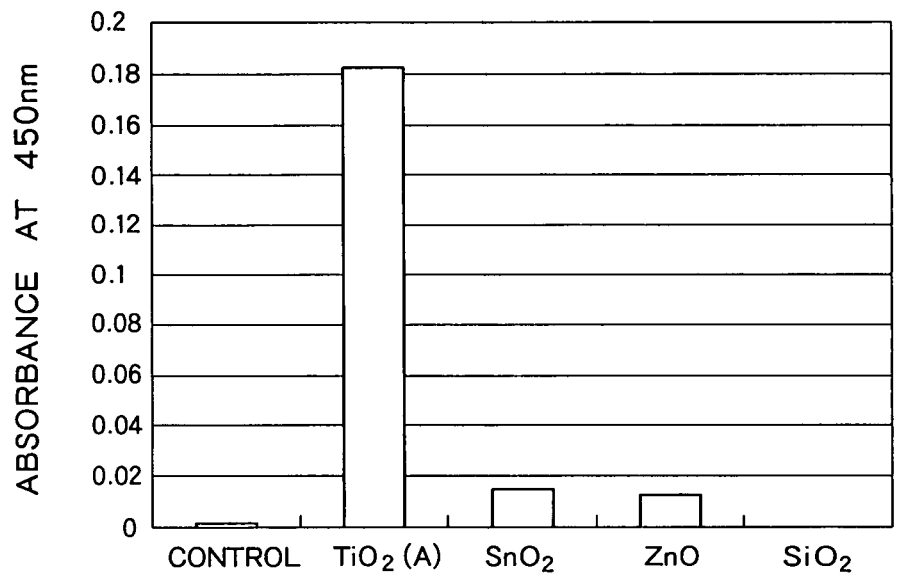
F I G. 3
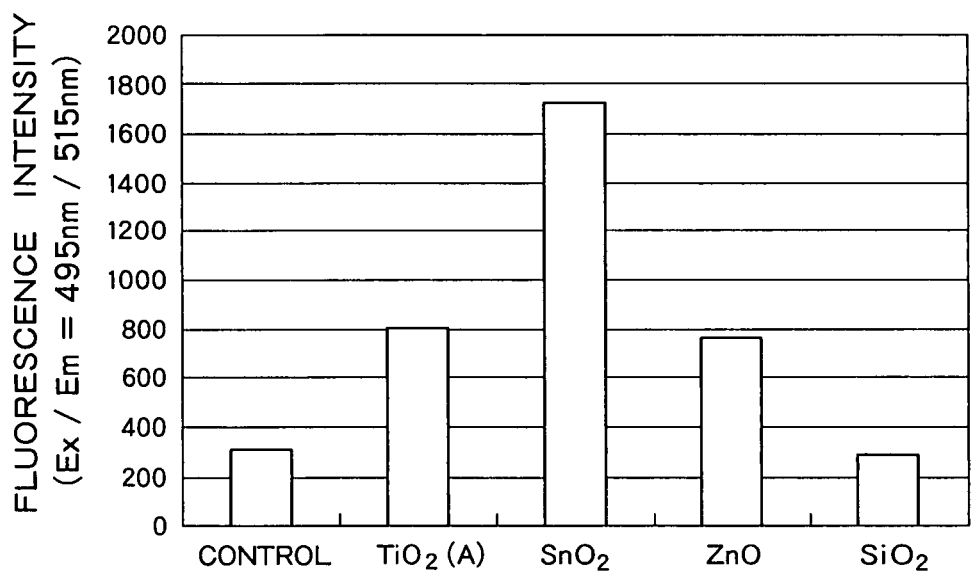
F I G. 4

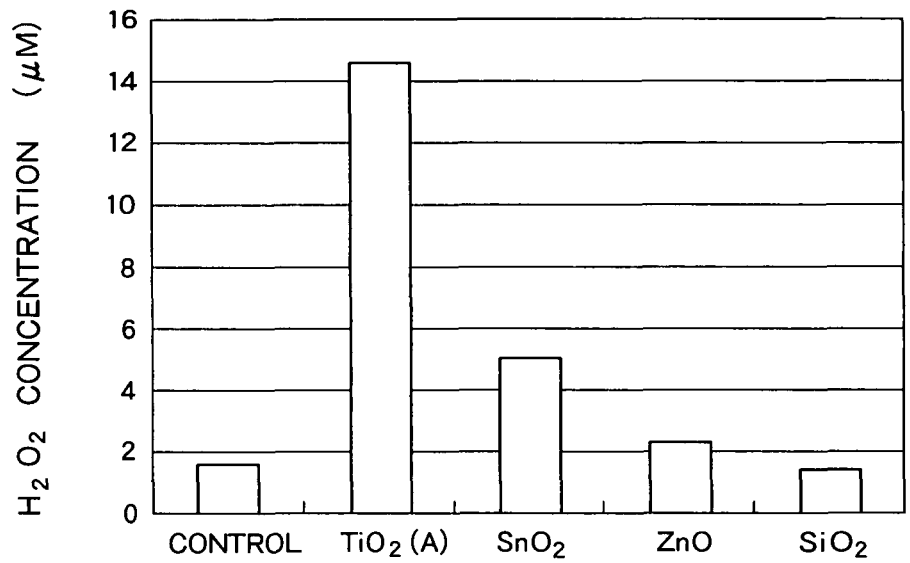
F I G. 5
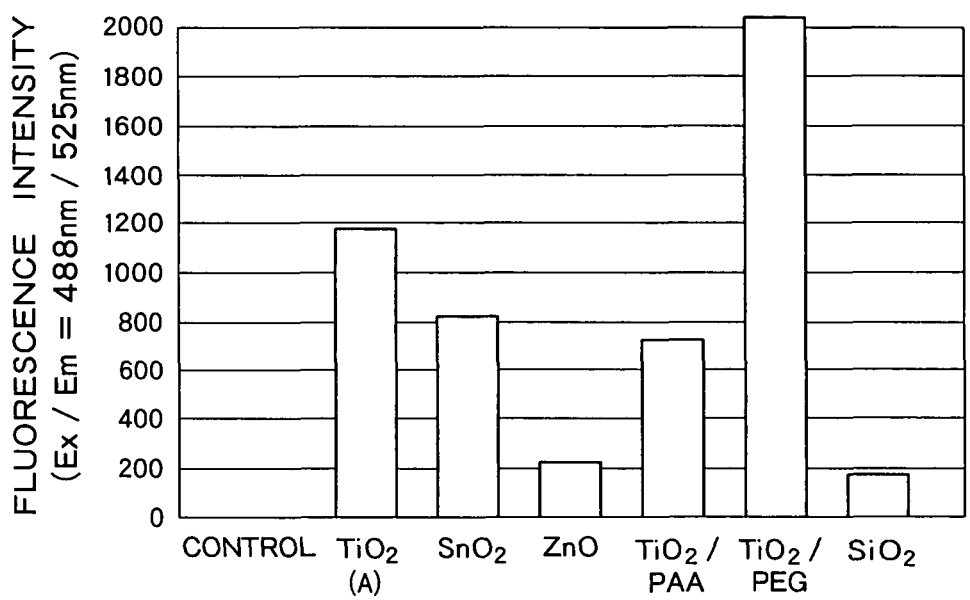
F I G. 6

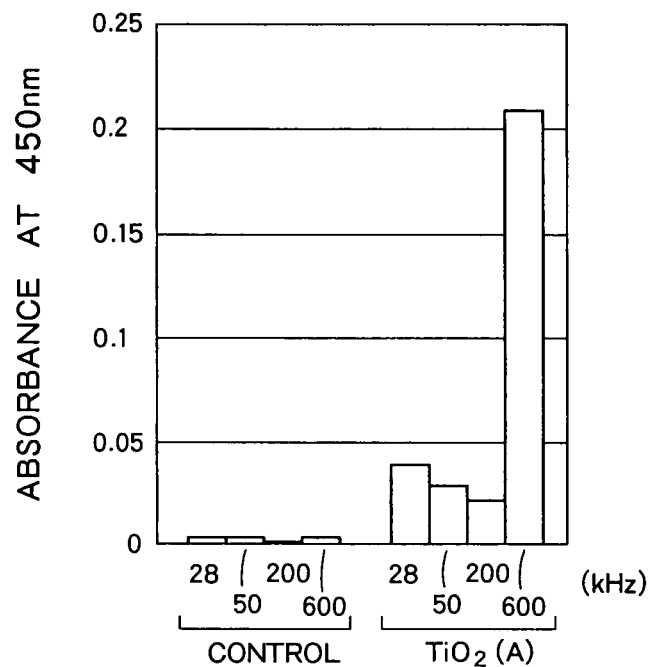
F I G. 7
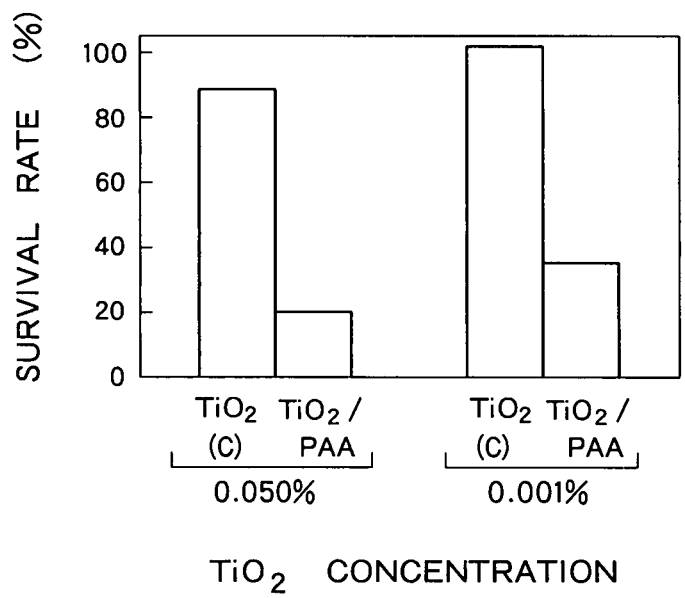
F I G. 8

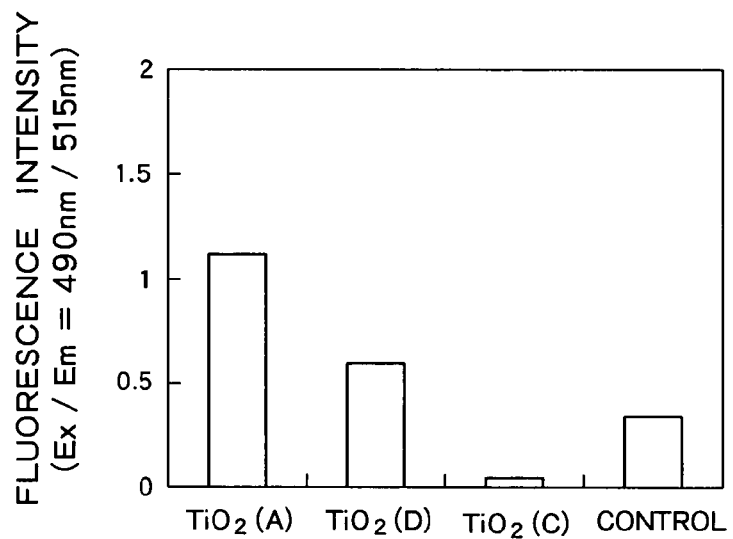
F I G. 9
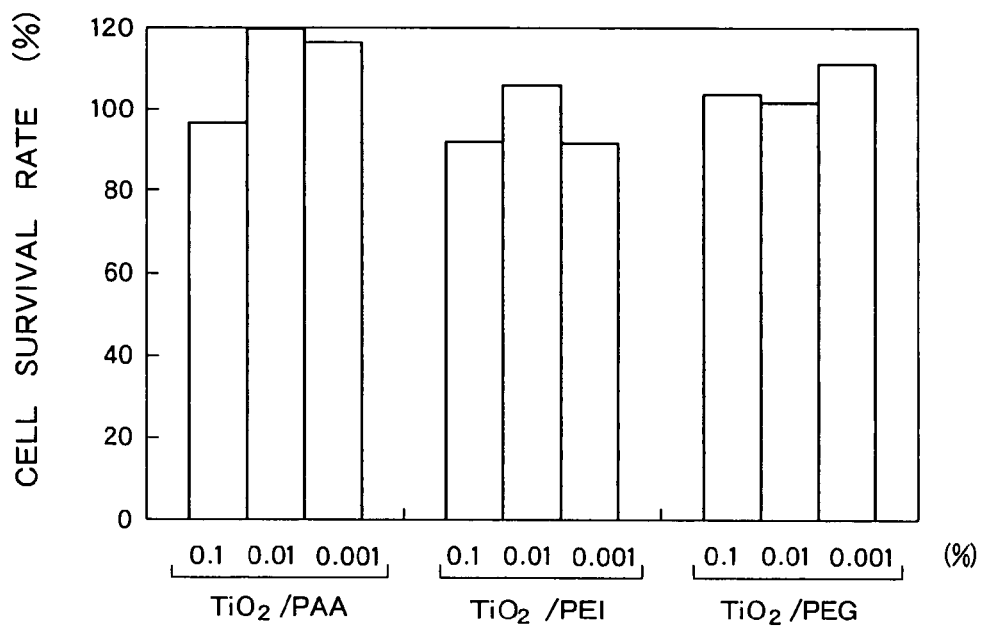
F I G. 10

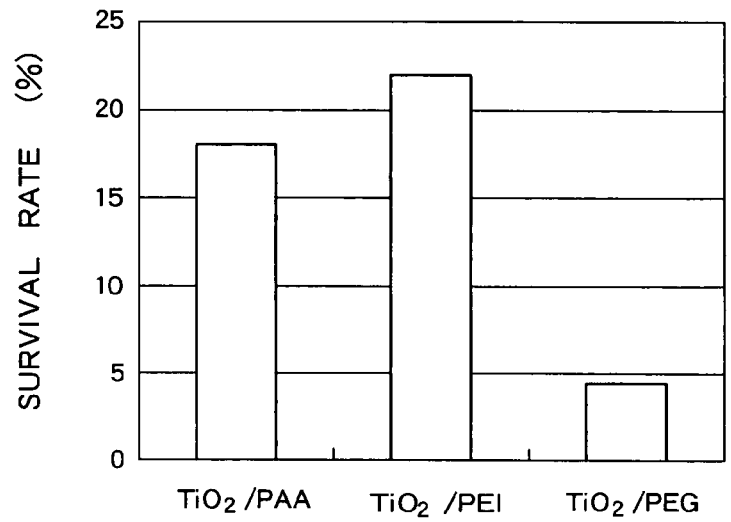
F I G. 11
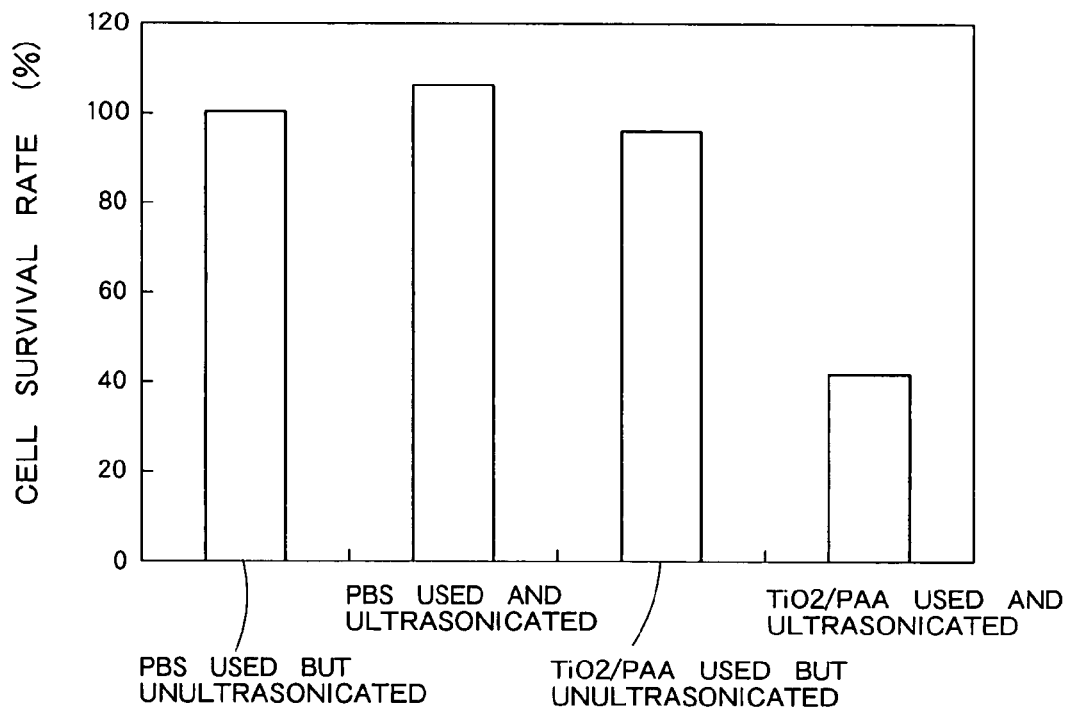
F I G. 12

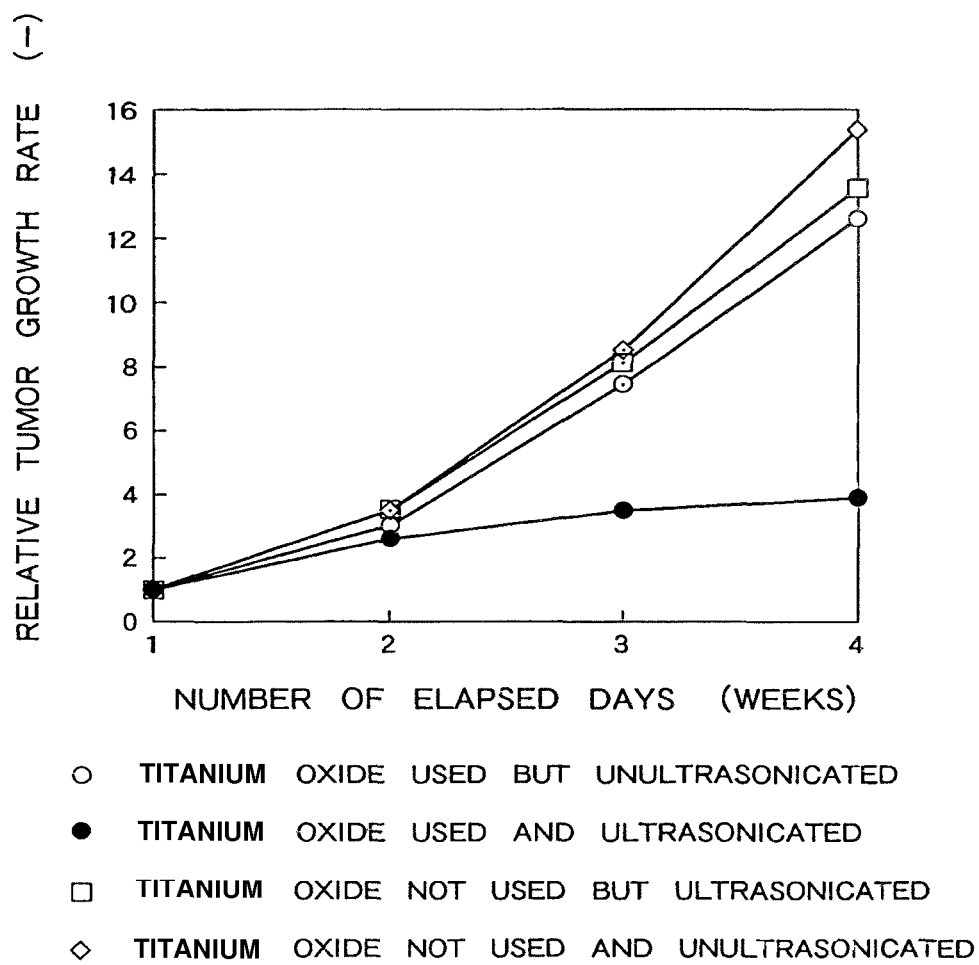
F I G. 13

ULTRASONIC CANCER TREATMENT ENHANCER AND CELL KILLER

CROSS-REFERENCE TO RELATED APPLICATIONS

The present application is a U.S. National phase of, and claims priority based on PCT/JP2006/321392, filed 26 Oct. 2006, which, in turn, claims priority from Japanese patent application 2005-311871, filed 26 Oct. 2005, Japanese patent application 2006-83757, filed 24 Mar. 2006, Japanese patent application 2006-171843, filed 21 Jun. 2006, and Japanese patent application 2006-246757, filed 12 Sep. 2006. The entire disclosure of each of the referenced priority documents is incorporated herein by reference.

BACKGROUND OF THE INVENTION

1. Field of the Invention

The present invention relates to an ultrasonic cancer treatment enhancer for enhancing ultrasonic cancer treatment by exposing an affected part to ultrasonic waves, and a cell killer which, upon exposure to ultrasonic waves, can be rendered cytotoxic and can kill target cells to be killed, such as cancer cells.

2. Background Art

In recent years, in cancer treatment, sonodynamic therapy, which is noninvasive and can efficiently treat an affected part, has been proposed from the viewpoint of simultaneously improving both therapeutic effect and QOL (quality of life) of patients. According to the sonodynamic therapy, an administered medicament, which is used in combination with ultrasonic waves, is rendered antitumor-active by ultrasonic irradiation to treat the tumor. A method using fullerene as an agent to be used in combination with ultrasonic therapy is known (see, for example, Japanese Patent Laid-Open No. 241307/2002 and WO 2002/66061). A method using pigment as an agent to be used in combination with ultrasonic therapy is also known (see, Japanese Patent Laid-Open No. 253836/2001, WO98/1131, and Japanese Patent Laid-Open No. 226654/2003). According to the above methods, treatment is carried out by exciting organic matter or fullerene, which produces radical species upon exposure to light, by ultrasonic effect.

On the other hand, a proposal has been made in which the photocatalytic activity of titanium oxide is utilized for cancer treatment. For example, the utilization of titanium oxide as a medical device (see Japanese Patent Laid-Open No. 357941/1992) and as a carrier for a drug delivery system (DDS) (see Japanese Patent Laid-Open No. 200050/2001 and U.S. Pat. No. 6,677,606) has been proposed.

Further, a technique has also been proposed in which titanium oxide having a particle size of 2 to 3 mm is exposed to ultrasonic waves of 35 to 42 kHz to generate hydroxy radicals which decompose organic matter (see, for example, Japanese Patent Laid-Open No. 26406/2003).

SUMMARY OF THE INVENTION

The present inventors have now found that, upon exposure of a certain type of semiconductor particles to ultrasonic waves of a specific frequency, the effect of treatment of cancer by ultrasonic irradiation can be significantly improved while ensuring a high level of safety. Further, the present inventors have also found that the effect of treating cancer can be further improved by using a drug delivery system in which the semiconductor particles are administered into the body of a patient and allowed to reach cancer cells followed by the application of ultrasonic waves of a specific frequency to an affected part.

Accordingly, an object of the present invention is to provide an ultrasonic cancer treatment enhancer and cell killer that can efficiently kill cells to be killed, such as cancer cells, while ensuring a high level of safety.

According to one aspect of the present invention, there is provided an ultrasonic cancer treatment enhancer comprising metal semiconductor particles.

According to another aspect of the present invention, there is provided a cell killer comprising metal semiconductor particles, the cell killer being convertible to a cytotoxin upon ultrasonic irradiation.

According to still another aspect of the present invention, there is provided a method for treating cancer, characterized by administering a cell killer to an animal including human, exposing cancer cells in the animal after the administration to ultrasonic waves to convert the cell killer to a cytotoxin, whereby the cytotoxin kills the cancer cells.

According to a further aspect of the present invention, there is provided use of the cell killer for producing an ultrasonic cancer treatment enhancer, wherein the ultrasonic cancer treatment enhancer is used in a method comprising administering the ultrasonic cancer treatment enhancer to an animal including human, then exposing cancer cells to ultrasonic waves to convert the cell killer to a cytotoxin, whereby the cytotoxin kills the cancer cells.

BRIEF DESCRIPTION OF THE DRAWINGS

FIG. 1 is a diagram showing the cell kill rates upon ultrasonic irradiation for one minute as measured for various particles in Example 4.

FIG. 2 is a diagram showing the cell survival rates as measured for test solutions containing $TiO_2$ particles ($TiO_2$/PAA) in various concentrations in Example 5.

FIG. 3 is a diagram showing the rises in absorbance through a reductive chromogenic reagent attributable to the generation of a superoxide anion upon ultrasonic irradiation as measured for various particles in Example 6.

FIG. 4 is a diagram showing the fluorescence intensities through a fluorescence reagent for active oxygen detection attributable to the generation of hydroxy radicals upon ultrasonic irradiation as measured for various particles in Example 7.

FIG. 5 is a diagram showing the rises in absorbance through TPM-PS oxidation attributable to the generation of hydrogen peroxide upon ultrasonic irradiation as measured for various particles in Example 8.

FIG. 6 is a diagram showing the fluorescence intensities through a fluorescence reagent for singlet oxygen detection attributable to the generation of singlet oxygen upon ultrasonic irradiation as measured for various particles in Example 9.

FIG. 7 is a diagram showing the rises in absorbance through a reductive chromogenic reagent attributable to the generation of a superoxide anion upon ultrasonic irradiation as measured for $TiO_2$ (A) in Example 10.

FIG. 8 is a diagram showing the cell survival rates upon ultrasonic irradiation for one minute as measured for various particles in Example 12.

FIG. 9 is a diagram showing the fluorescence intensities through a fluorescence reagent for active oxygen detection attributable to the generation of hydroxy radicals upon ultrasonic irradiation as measured for various particles in Example 13.

FIG. 10 is a diagram showing the cell survival rate as measured for test solutions containing $TiO_2$ particles in various concentrations in Example 14.

FIG. 11 is a diagram showing the cell kill rates upon ultrasonic irradiation for one minute as measured for various particles in Example 15.

FIG. 12 is a diagram showing the cell survival rates upon ultrasonic irradiation for 2 minutes (ultrasonicated) and ultrasonic irradiation-free (not ultrasonicated or unultrasonicated) cells as measured for $TiO_2$/PAA particles and a PBS buffer solution in Example 16. As used in this application "ultrasonicated" means exposing to ultrasonic radiation.

FIG. 13 is a diagram showing the changes with time in relative tumor growth rate of mice as measured in Example 17.

DETAILED DESCRIPTION OF THE INVENTION

Ultrasonic Cancer Treatment Enhancer

The ultrasonic cancer treatment enhancer in a first embodiment of the present invention comprises metal semiconductor particles. Metal semiconductor particles usable in the present invention may be various metal semiconductor particles without limitation so far as they are activated upon ultrasonic irradiation to kill or destruct cancer cells. Although the mechanism through which certain metal semiconductor particles are activated upon ultrasonic irradiation to kill or destruct cells, has not been fully elucidated yet, the above effect can be expected to be attained at least when the metal semiconductor particles can produce radical species upon ultrasonic irradiation.

That is, the biological killing effect provided by the metal semiconductor particles can be realized by producing radical species by ultrasonic irradiation. Specifically, the biological killing effect provided by the metal semiconductor particles is considered attributable to a qualitative/quantitative increase in radical species. The reason for this is considered as follows. The following reason, however, is merely a hypothetical, and the present invention is not limited by the following description. Specifically, when only ultrasonic irradiation is adopted, hydrogen peroxide and hydroxy radicals are generated in the system. According to the finding by the present inventors, however, the production of hydrogen peroxide and hydroxy radicals is promoted in the presence of semiconductor particles such as titanium oxide. Further, in the presence of these semiconductor particles, particularly in the presence of titanium oxide, it seems that the production of superoxide anion and singlet oxygen is promoted. The specific production of these radical species is a phenomenon observed during the ultrasonic irradiation when fine particles on nanometer order are used. This effect is considered to be a specific phenomenon caused by ultrasonic waves in the presence of metal semiconductor fine particles.

In a preferred embodiment of the present invention, it is preferred to use metal semiconductor particles having photosensitive properties as the metal semiconductor particles. More preferred are metal semiconductor particles having photocatalytic activity and quantum dots which emit light by quantum effect. Here the metal semiconductor particles having photocatalytic activity are particles of a photometal semiconductor that causes charge separation upon exposure to light energy. The quantum dot is a structure characterized in that, even in such a state that thermal excitation is present at room temperature or the like due to discrete energy distribution of electron carrier, the transition of carriers occur discontinuously between quantum levels and, consequently, leading to sharp luminescence. Such particles can be satisfactorily activated upon ultrasonic irradiation to kill cells. Specific examples of these metal semiconductor particles include metal oxides such as $TiO_2$, $ZnO$, $WO_3$, $SnO_2$, $Fe_2O_3$, $In_2O_3$, $BaTiO_3$, $TiO_3$, $SrTiO_3$, $Nb_2O_5$, and $Ta_2O_5$; metal sulfides such as $CdS$, $MoS_2$ and $ZnS$; and composite metal semiconductors such as $SiC$, $CdSe$ and $InGaP$. These metal semiconductor particles are photosensitive. Since, however, the metal semiconductor particles are not a photosensitizer such as fullerene or pigment, any problem of photohypersensitive diseases does not take place at the stage of treatment after administration to a patient. Thus, a very high level of safety can be realized.

In a preferred embodiment of the present invention, metal semiconductor particles having photocatalytic activity may be used as the metal semiconductor particles. Preferred examples of such metal semiconductor particles include particles of $TiO_2$, $ZnO$, $SnO_2$, $WO_3$, $In_2O_3$, $SrTiO_3$, $Nb_2O_5$, and $Ta_2O_5$. Particles of $TiO_2$ are more preferred.

In a preferred embodiment of the present invention, quantum dots may be used as the metal semiconductor particles. Preferred examples include $CdSe$, $CdS$, $CdTe$, $ZnS$, $ZnSe$, $InGaP$, and $ZnTe$ and mixtures thereof.

In a preferred embodiment of the present invention, the particle diameter of the metal semiconductor particles is 50 to 200 nm, more preferably 50 to 150 nm. In this particle diameter range, upon administration into the body of a patient aiming at arrival at a tumor, as in a drug delivery system, the metal semiconductor particles can efficiently reach and be accumulated in the cancer tissue by virtue of EPR effect. Accordingly, the cancer tissue can be highly efficiently killed or destructed by ultrasonic irradiation.

In another preferred embodiment of the present invention, when the diameter of the metal semiconductor particles is less than 50 nm, for example, several nanometers, the EPR effect can also be attained by connecting the metal semiconductor particles to each other through a multifunctional linker to increase the apparent size. This embodiment is particularly useful when quantum dots are used as the metal semiconductor particles. Specifically, although the quantum dots generally have a particle diameter of 2 to 10 nm, a high cancer treatment effect can be attained by EPR effect by aggregating or binding a plurality of quantum dots to form secondary particles having a particle diameter of 50 to 150 nm. In still another preferred embodiment of the present invention, in order to utilize the EPR effect, the metal semiconductor particles can also be included in a drug inclusion such as liposome. Further, when a biological element such as antibody is imparted to the composite particles thus obtained, a higher effect of targeting to the tumor than the EPR effect can be attained.

The metal semiconductor particles usable in the present invention include not only a single type of metal semiconductor particles but also a mixture or composite of a plurality types of metal semiconductor particles. Specific examples thereof include a composite of titanium oxide nanoparticles with iron oxide nanoparticles, a composite of titanium oxide nanoparticles with platinum, and silica-coated titanium oxide.

In a preferred embodiment of the present invention, a polymer or a biopolymer is bonded to the surface of metal semiconductor particles. According to this construction, even when an inherently solid and neutral semiconductor is used, dispersing of an ultrasonic cancer treatment enhancer composed mainly of semiconductor particles can be realized and, consequently, safe administration in a body environment can be realized. The polymer to be bonded to the surface of the metal semiconductor particles may be any hydrophilic polymer.

In a preferred embodiment of the present invention, it is preferred to use, as the polymer to be bonded to the surface of the metal semiconductor particles, carboxyl group-containing polymers, for example, carboxymethyl starch, carboxymethyl dextran, carboxymethylcellulose, polycarboxylic acids, and copolymers comprising carboxyl group units. Polycarboxylic acids such as polyacrylic acid and polymaleic acid; and copolymers such as copolymers of acrylic acid/maleic acid monomers or acrylic acid/sulfonic acid monomers are more preferred from the viewpoint of hydrolyzability and solubility of hydrophilic polymers. Polyacrylic acid is still more preferred. When the carboxyl group-containing polymer is bonded to the surface of the metal semiconductor particles, the particles are negatively charged. Accordingly, a high level of dispersion of the particles can be attained, and, at the same time, biological molecules and medicaments can be easily immobilized on the particles. Therefore, the semiconductor particles are also suitable for systemic administration, for example, through instillation. Consequently, metal semiconductor particles having polyacrylic acid bonded on its surface are suitable for the cancer treatment of the inside of organs, and, when (biological) molecules having high affinity for specific cells or medicaments have been immobilized, the metal semiconductor particles are particularly suitable, as metal semiconductor particles having higher affinity, for use in targeting therapy for targeting to an affected part.

In a preferred embodiment of the present invention, it is preferred to use, as the polymer to be bonded to the surface of the metal semiconductor particles, cationic polymers, for example, amines having a weight average molecular weight in the range of 1000 to 100000. Polyamino acids, polypeptides, polyamines, and amine unit-containing copolymers are more preferred. Further, from the viewpoint of the hydrolyzability and solubility of water soluble polymers, polyamines such as polyethyleneimine, polyvinylamine, and polyallylamine are more preferred, and polyethyleneimine is most preferred. Upon binding of the cationic polymer to the surface of the metal semiconductor particles, the particles are positively charged. Accordingly, a high level of dispersion of the particles can be realized, and, at the same time, the positively charged particles are likely to be rapidly adsorbed and incorporated in cells. Thus, such semiconductor particles are suitable for injection or topical administration by coating. Consequently, the metal semiconductor particles having polyethyleneimine bonded on its surface are particularly suitable for the treatment of superficial cancers such as skin cancers and early cancers.

In a preferred embodiment of the present invention, it is preferred to use, as the polymer to be bonded to the surface of the metal semiconductor particles, nonionic polymers, for example, polyethylene glycol, polyvinyl alcohol, polyethylene oxide, dextran, or their copolymers. Polyethylene glycol is more preferred. Upon binding of the nonionic polymer onto the surface of the metal semiconductor particles, the particles are dispersed by hydration without electrification and thus stably stay within the body (in blood) for a long period of time, are likely to be accumulated in a cancer tissue, and are also suitable for systemic administration. Accordingly, the metal semiconductor particles coated with polyethylene glycol are particularly suitable for the treatment of a broad range of cancers from superficial cancers to deep-part cancers.

In a preferred embodiment of the present invention, the metal semiconductor particles are dispersed in a solvent. This can allow the metal semiconductor particles to be efficiently administered into the patient's body by various methods such as instillation, injection, or coating. The dispersion liquid preferably has neutral liquidity from the viewpoint of safety and is more preferably physiological saline.

Cell Killer

In a second embodiment of the present invention, there is provided a cell killer comprising metal semiconductor particles, the cell killer being convertible to a cytotoxin upon ultrasonic irradiation. The cell killer can destruct or kill cells by being administered into the body and exposed to ultrasonic waves to become cytotoxic. In this case, the cell killer can destruct or kill cells to be killed not only in vivo but also in vitro. In this embodiment, the target cells to be killed are not particularly limited but are preferably cancer cells. Further, in this embodiment, the cytotoxin is preferably produced by radical species produced by the semiconductor particles upon ultrasonic irradiation.

In a preferred embodiment of the present invention, the cell killer comprises at least one type of semiconductor particles selected from the group consisting of $TiO_2$, $SnO_2$, $ZnO$ and $CdSe$. $TiO_2$ is more preferred. In a preferred embodiment of the present invention, these semiconductor particles, when exposed to ultrasonic waves of 400 kHz to 20 MHz, can be rendered cytotoxic. The cell killer can kill cells by being administered into the body and exposed to ultrasonic waves to become cytotoxic. The cell killer can kill cells to be killed not only in vivo but also in vitro. In the present invention, the target cells to be killed are not particularly limited. However, cancer cells are preferred. That is, the cell killer according to the present invention can be activated upon ultrasonic irradiation to kill cancer cells. Since the semiconductor particles are not a photosensitizer such as fullerene or pigment, any problem of photohypersensitive diseases does not take place at the stage of treatment after administration to a patient, and, thus, a very high level of safety can be realized.

The effect of killing cells by activation of the semiconductor particles upon ultrasonic irradiation can be realized by producing radical species by ultrasonic irradiation. Specifically, the biological killing effect provided by the semiconductor particles is considered attributable to a qualitative/quantitative increase in radical species. The reason for this is considered as follows. The following reason, however, is merely a hypothetical, and the present invention is not limited by the following description. Specifically, when only ultrasonic irradiation is adopted, hydrogen peroxide and hydroxy radicals are generated in the system. According to the finding by the present inventors, however, the production of hydrogen peroxide and hydroxy radicals is promoted in the presence of semiconductor particles such as titanium oxide. Further, in the presence of these semiconductor particles, particularly in the presence of titanium oxide, it seems that the production of superoxide anion and singlet oxygen is promoted. When fine particles on nanometer order are used, the specific production of these radical species is a phenomenon significantly observed in the ultrasonic irradiation at an ultrasonic irradiation frequency in the range of 400 kHz to 20 MHz, preferably in the range of 600 kHz to 10 MHz, more preferably in the range of 1 MHz to 10 MHz. This effect is considered to be a specific phenomenon caused by ultrasonic waves in the presence of metal semiconductor fine particles.

In a preferred embodiment of the present invention, the particle diameter of the semiconductor particles is 20 to 200 nm, more preferably 50 to 200 nm, still more preferably 50 to 150 nm. In this particle diameter range, upon administration into the body of a patient aiming at arrival at a tumor, as in a drug delivery system, the semiconductor particles can efficiently reach and be accumulated in the cancer tissue by virtue of EPR effect, and, as described above, upon ultrasonic irradiation of 400 kHz to 20 MHz, specific production of radical species takes place. Accordingly, the cancer tissue can be highly efficiently killed by ultrasonic irradiation.

In another preferred embodiment of the present invention, when the diameter of the semiconductor particles is less than 50 nm, for example, several nanometers, the EPR effect can also be attained by increasing the apparent size. Specifically, a higher level of cancer therapeutic effect can be realized by the EPR effect, for example, when semiconductor particles are bonded to each other, for example, through a multifunctional linker so as to take the form of secondary particles having a particle diameter of 50 to 150 nm. In another preferred embodiment of the present invention, in order to utilize the EPR effect, the semiconductor particles can also be included in a drug inclusion such as liposome.

The particle diameter of the semiconductor particles according to the present invention can be measured by a dynamic light scattering method. Specifically, the particle diameter of the semiconductor particles according to the present invention can be provided as a value expressed in terms of Z-average size obtained by a cumulant analysis with a particle size distribution measuring apparatus (Zetasizer Nano, manufactured by Malvern Instruments Ltd.).

In a preferred embodiment of the present invention, when a biological element such as antibody is further imparted to the semiconductor particles, a higher effect of targeting to the tumor than the EPR effect can be attained.

The semiconductor particles usable in the present invention include not only a single type of semiconductor particles but also a mixture or composite of a plurality types of semiconductor particles. Specific examples thereof include a composite of titanium oxide nanoparticles with iron oxide nanoparticles, a composite of titanium oxide nanoparticles with platinum, and silica-coated titanium oxide.

In a preferred embodiment of the present invention, a polymer and/or a biopolymer are bonded to the surface of semiconductor particles. According to this construction, even when an inherently solid and neutral semiconductor is used, dispersing of a cell killer composed mainly of semiconductor particles can be realized and, consequently, safe administration in a body environment can be realized. The polymer to be bonded to the surface of the semiconductor particles may be any hydrophilic polymer. The form of bonding between the semiconductor particles and the polymer and/or biopolymer is not particularly limited so far as, from the viewpoint of ensuring the retentivity in blood, the dispersibility is ensured 24 to 72 hr after administration into the body. A covalent bond is preferred as the form of bonding because the dispersion stability under physiological conditions is excellent and, at the same time, even after the ultrasonic irradiation, liberation of the polymer does not take place with no significant damage to normal cells.

In a preferred embodiment of the present invention, it is preferred to use, as the polymer to be bonded to the surface of the semiconductor particles, anionic polymers, for example, carboxymethyl starch, carboxymethyl dextran, carboxymethylcellulose, polycarboxylic acids, and carboxyl group-containing polymers, such as copolymers comprising carboxyl group units. Polycarboxylic acids such as polyacrylic acid and polymaleic acid; and copolymers such as copolymers of acrylic acid/maleic acid monomers or acrylic acid/sulfonic acid monomers are more preferred from the viewpoint of hydrolyzability and solubility of hydrophilic polymers. Polyacrylic acid is still more preferred. When the anionic polymer is bonded to the surface of the semiconductor particles, the particles are negatively charged. Accordingly, a high level of dispersion of the particles can be attained, and, at the same time, the immobilization of biological molecules or medicaments onto the semiconductor particles through the functional group of the polymer can also render the semiconductor particles suitable for systemic administration through instillation or the like. Consequently, semiconductor particles having polyacrylic acid bonded on its surface are suitable for the cancer treatment of the inside of organs, and, when (biological) molecules having high affinity for specific cells or medicaments have been immobilized, the semiconductor particles are particularly suitable, as semiconductor particles having higher affinity, for use in targeting therapy for targeting to an affected part. The zeta potential of the semiconductor particle composite to which the anionic polymer has been immobilized is preferably −50 to −20 mV. Within this range, the dispersibility of the particles can easily be ensured by the repulsion of negative charges to reduce the tendency toward the formation of aggregates. Accordingly, there is no possibility that secondary negative effect such as occlusion of blood vessels takes place after the administration.

In a preferred embodiment of the present invention, it is preferred to use, as the polymer to be bonded to the surface of the semiconductor particles, cationic polymers, for example, amines having a weight average molecular weight in the range of 1000 to 100000. Polyamino acids, polypeptides, polyamines, and amine unit-containing copolymers are more preferred. Further, from the viewpoint of the hydrolyzability and solubility of water soluble polymers, polyamines such as polyethyleneimine, polyvinylamine, and polyallylamine are more preferred, and polyethyleneimine is most preferred. Upon binding of the cationic polymer to the surface of the semiconductor particles, the particles are positively charged. Accordingly, a high level of dispersion of the particles is realized, and, at the same time, the positively charged particles are likely to be rapidly adsorbed and incorporated in cells. Thus, such semiconductor particles are suitable for injection or topical administration by coating. Consequently, the semiconductor particles having a surface to which polyethyleneimine has been bonded are particularly suitable for the treatment of superficial cancers such as skin cancers and early cancers. The zeta potential of the semiconductor particle composite to which the cationic polymer has been immobilized is preferably +20 to +50 mV. Within this range, the dispersibility of the particles can easily be ensured by the repulsion of positive charges and, thus, this semiconductor particle composite is suitable for topical administration.

In a preferred embodiment of the present invention, it is preferred to use, as the polymer to be bonded to the surface of the semiconductor particles, polymers containing nonionic hydrophilic groups (hydroxyl group and/or polyoxyalkylene group), for example, polyethylene glycol, polyvinyl alcohol, polyethylene oxide, dextran, or their copolymers. Polyethylene glycol is more preferred. Upon binding of the nonionic polymer onto the surface of the semiconductor particles, the particles are dispersed by hydration without electrification and thus stably stay within the body (in blood) for a long period of time, are likely to be accumulated in a cancer tissue, and are also suitable for systemic administration. Accordingly, the semiconductor particles coated with polyethylene glycol are particularly suitable for the treatment of a broad range of cancers from superficial cancers to deep-part cancers. The zeta potential of the semiconductor particle composite to which the nonionic hydrophilic group-containing polymer has been immobilized is preferably −20 to +20 mV. Within this range, blood proteins are less likely to be electrostatically adsorbed. Accordingly, for example, incorporation in a reticuloendothelial system, renal excretion, and liver uptake can easily be avoided, and retentivity in blood sufficient for arrival at the target site (tumor) can be ensured.

In a preferred embodiment of the present invention, the semiconductor particles are preferably dispersed in a solvent. This can allow the semiconductor particles to be efficiently administered into the patient's body by various methods such as instillation, injection, or coating. The dispersion liquid preferably has neutral liquidity from the viewpoint of safety and is more preferably physiological saline. The content of the semiconductor particles in the dispersion is preferably 0.001 to 1% by weight, more preferably 0.001 to 0.1% by weight. Within this range, the particles can be effectively accumulated in the affected part (tumor) 24 to 72 hr after the administration. Specifically, the particles are likely to be accumulated in the affected part (tumor), and the dispersibility of the particles in blood is also ensured to reduce the tendency toward the formation of aggregates. Accordingly, there is no possibility that secondary negative effect such as occlusion of blood vessels takes place after the administration.

Treating Method

The ultrasonic cancer treatment enhancer and cell killer according to the present invention can be administered into the body of a patient by various methods, for example, instillation, injection or coating. It is particularly preferred to use the ultrasonic cancer treatment enhancer and cell killer through an intravenous or subcutaneous administration from the viewpoint of reducing the patient's burden by the so-called DDS-like therapy utilizing EPR effect by the size of particles and the retentivity in blood. The enhancer or cell killer administered into the body reaches the cancer tissue and is accumulated as in the drug delivery system. Thereafter, the cancer tissue, in which the enhancer or cell killer has been accumulated, is ultrasonicated. The frequency of ultrasonic waves used is preferably, 20 kHz to 20 MHz, more preferably 400 kHz to 20 MHz, still more preferably 600 kHz to 10 MHz, most preferably 1 MHz to 10 MHz, from the viewpoints of cell killing effect and safety. The ultrasonic irradiation time should be properly determined by taking into consideration the position and size of the cancer tissue as a treatment object and is not particularly limited. Thus, the patient's cancer tissue can be killed by ultrasonic waves with high efficiency to realize high cancer therapeutic effect. The ultrasonic waves are able to reach the deep part in the body from the outside of the body, and the use of a combination of the ultrasonic waves with the enhancer or cell killer according to the present invention can realize the treatment, in a noninvasive state, of an affected part or target site present in the deep part in the body. Further, since the enhancer or cell killer according to the present invention is accumulated in the affected part or target site, very weak-intensity ultrasonic waves on such a level that does not adversely affect normal cells around the affected part or target site, can be allowed to act topically only on the place where the enhancer or cell killer according to the present invention has been accumulated.

In a preferred embodiment of the present invention, the metal semiconductor particles are more preferably $TiO_2$. However, the utilization of the photocatalytic activity of the metal semiconductor particles in the treatment of cancer is also proposed. In this case, the treatment of the affected part or target site can be carried out by ultraviolet irradiation, and the arrival depth irradiation is 2 mm from the body superficial part. On the other hand, for example, when the body is diagnosed by ultrasonic irradiation, even the diagnosis of the body in its part distant by not less than 2 mm from the superficial part of the body is possible. Accordingly, since the ultrasonic waves can arrive from the outside of the body at a deep part in the body, the use of a combination of the ultrasonic waves with the enhancer according to the present invention can realize the treatment, in a noninvasive state, of an affected part or target site present in a deep part in the body.

In a preferred embodiment of the present invention, preferred application sites includes an organ which cannot be excised without difficulties, specifically, pancreatic cancer, bladder cancer, and cerebral tumor.

The ultrasonic irradiation part is not particularly limited. In a preferred embodiment of the present invention, however, in order to attain a better effect, a method may be adopted in which an ultrasonic irradiation part is installed in an instrument accessible to the affected part or target site, such as an endoscope or catheter, so that the ultrasonic waves can be applied directly to the affected part or target site. Further, when the contemplated organ cannot be excised without difficulties, or from the viewpoint of QOL of patients, the ultrasonic waves may be applied in a noninvasive state from the outside of the body. Specifically, a method may be adopted in which ultrasonic waves are applied from the abdominal part to a superficial cancer in a digestive organ and are allowed to reach the affected part to kill the cancer tissue.

EXAMPLES

Example 1

Preparation of Polyacrylic Acid-Bonded Titanium Oxide ($TiO_2$/PAA) Particles

Titanium tetraisopropoxide (3.6 g) was mixed with 3.6 g of isopropanol, and the mixture was added dropwise to 60 ml of ultrapure water under ice cooling for hydrolysis. After the dropwise addition, the mixture was stirred at room temperature for 30 min. After the stirring, 1 ml of 12 N nitric acid was added dropwise thereto, and the mixture was stirred at 80° C. for 8 hr for peptization. After the completion of the peptization, the mixture was filtered through a 0.45-µm filter and was subjected to solution exchange with a desalination column (PD10, manufactured by Amersham Pharmacia Bioscience) to prepare an anatase-type titanium oxide sol having a solid content of 1%. This dispersion liquid was placed in a 100-ml vial bottle and was ultrasonicated at 200 kHz for 30 min. The average dispersed particle diameter before the ultrasonication and that after the ultrasonication were 36.4 nm and 20.2 nm, respectively. After the ultrasonication, the solution was concentrated to prepare a titanium oxide sol (anatase type) having a solid content of 20%.

The titanium oxide sol (0.75 ml) thus obtained was dispersed in 20 ml of dimethylformamide (DMF), and 10 ml of DMF containing 0.2 g of polyacrylic acid (average molecular weight: 5000, manufactured by Wako Pure Chemical Industries, Ltd.) dissolved therein was added to the dispersion, followed by stirring for mixing. The solution was transferred to a hydrothermal reaction vessel, and a reaction was allowed to proceed at 150° C. for 6 hr. After the completion of the reaction, the reaction vessel was cooled to a temperature of 50° C. or below. The solution was then taken out of the reaction vessel. Water (80 ml) was then added to the solution, and the mixture was stirred for mixing. After the removal of DMF and water by an evaporator, 20 ml of water was again added to prepare a polyacrylic acid-modified titanium oxide aqueous solution. Thereafter, 1 ml of 2 N hydrochloric acid was added to precipitate titanium oxide particles, and the mixture was centrifuged, followed by the removal of the supernatant to separate the polyacrylic acid remaining unreacted. Water was again added to the residue for washing, the mixture was centrifuged, and the water was then removed. After the addition of 10 ml of a 50 mM phosphate buffer solution (pH 7.0), the mixture was ultrasonicated at 200 kHz for 30 min to disperse titanium oxide particles. After the ultrasonication, the dispersion liquid was filtered through a 0.45-μm filter to prepare a polyacrylic acid-modified titanium oxide sol having a solid content of 1.5%. The dispersed particle diameter of the polyacrylic acid-modified titanium oxide fine particles (anatase type) thus obtained was measured with Zetasizer Nano ZS (manufactured by SYSMEX CORPORATION). As a result, it was found from the cumulant method analysis that the average dispersed particle diameter was 45.5 nm. This measurement was carried out by charging 0.75 ml of a dispersion liquid containing polyethyleneimine-bonded titanium oxide fine particles in a zeta potential measurement cell, setting various parameters of the solvent to the same values as water, and measuring the dispersed particle diameter at 25° C. by a dynamic light scattering method.

Example 2

Preparation of Polyethyleneimine-Bonded Titanium Oxide ($TiO_2$/PEI) Particles

Titanium tetraisopropoxide (3.6 g) was mixed with 3.6 g of isopropanol, and the mixture was added dropwise to 60 ml of ultrapure water under ice cooling for hydrolysis. After the dropwise addition, the mixture was stirred at room temperature for 30 min. After the stirring, 1 ml of 12 N nitric acid was added dropwise thereto, and the mixture was stirred at 80° C. for 8 hr for peptization. After the completion of the peptization, the mixture was filtered through a 0.45-μm filter and was subjected to solution exchange with a desalination column (PD-10, manufactured by Amersham Pharmacia Bioscience) to prepare an acidic titanium oxide sol having a solid content of 1%. This dispersion liquid was placed in a 100-ml vial bottle and was ultrasonicated at 200 kHz for 30 min. The average dispersed particle diameter before the ultrasonication and that after the ultrasonication were 36.4 nm and 20.2 nm, respectively. After the ultrasonication, the solution was concentrated to prepare a titanium oxide sol having a solid content of 20%.

The titanium oxide sol (0.75 ml) thus obtained was dispersed in 20 ml of dimethylformamide (DMF), and 10 ml of DMF containing 450 mg of polyethyleneimine (average molecular weight: 10000, manufactured by Wako Pure Chemical Industries, Ltd.) was added to the dispersion liquid, and the mixture was stirred for mixing. The solution was transferred to a hydrothermal reaction vessel (HU-50, manufactured by SAN-AI Science Co. Ltd.), and a reaction was allowed to proceed at 150° C. for 6 hr. After the completion of the reaction, the reaction vessel was cooled to a temperature of 50° C. or below. Isopropanol in an amount of twice the amount of the reaction mixture was added thereto to precipitate polyethyleneimine-bonded titanium oxide fine particles, and the mixture was centrifuged followed by the removal of the supernatant to separate the polyethyleneimine remaining unreacted. Thereafter, 70% ethanol was added for washing, the mixture was centrifuged, and ethanol was then removed. After the addition of 10 ml of distilled water, the mixture was ultrasonicated at 200 kHz for 30 min to disperse polyethyleneimine-bonded titanium oxide fine particles. After the ultrasonic treatment, the dispersion liquid was filtered through a 0.45-μm filter to prepare a dispersion liquid of polyethyleneimine-bonded titanium oxide fine particles having a solid content of 1.5%. The dispersed particle diameter of the polyethyleneimine-bonded titanium oxide fine particles thus obtained was measured with Zetasizer Nano ZS (manufactured by SYSMEX CORPORATION). As a result, it was found that the average particle diameter of the polyethyleneimine-bonded titanium oxide fine particles was 67.7 nm. This measurement was carried out by charging 0.75 ml of a dispersion liquid containing polyethyleneimine-bonded titanium oxide fine particles in a zeta potential measurement cell, setting various parameters of the solvent to the same values as water, and measuring the dispersed particle diameter at 25° C. by a dynamic light scattering method.

Example 3

Preparation of Polyethylene Glycol-Bonded Titanium Oxide ($TiO_2$/PEG) Particles Titanium tetraisopropoxide (3.6 g) was mixed with 3.6 g of isopropanol, and the mixture was added dropwise to 60 ml of ultrapure water under ice cooling for hydrolysis. After the dropwise addition, the mixture was stirred at room temperature for 30 min. After the stirring, 1 ml of 12 N nitric acid was added dropwise thereto, and the mixture was stirred at 80° C. for 8 hr for peptization. After the completion of the peptization, the mixture was filtered through a 0.45-μm filter and was subjected to solution exchange with a desalination column (PD-10, manufactured by Amersham Pharmacia Bioscience) to prepare an acidic titanium oxide sol having a solid content of 1%. This titanium oxide sol was placed in a 100-ml vial bottle and was ultrasonicated at 200 kHz for 30 min in an ultrasonic generator MIDSONIC 200 (manufactured by KAIJO Corporation). The average dispersed particle diameter after the ultrasonication was measured by diluting the ultrasonicated sol with 12 N nitric acid by a factor of 1000, charging 0.1 ml of the dispersion liquid in a quartz measurement cell, setting various parameters of the solvent to the same values as water, and measuring the dispersed particle diameter at 25° C. by a dynamic light scattering method with Zetasizer Nano ZS (manufactured by SYSMEX CORPORATION). As a result, it was found that the dispersed particle diameter was 20.2 nm. The titanium oxide sol was concentrated at a temperature of 50° C. using an evaporating dish to finally prepare an acidic titanium oxide sol having a solid content of 20%.

Next, 5 ml of water was added to 1 g of a copolymer of polyoxyethylene-monoallyl-monomethyl ether with maleic anhydride (average molecular weight; 33,659, manufactured by Nippon Oils & Fats Co., Ltd.). The mixture was hydrolyzed, and the hydrolyzate was then lyophilized. After the completion of the reaction, the reaction product was dissolved in 5 ml of a dimethylformamide (DMF) solution to prepare a 200 mg/ml polyethylene glycol solution. The polyethylene glycol solution (1.875 ml) thus obtained was added to 27.725 ml of a DMF solution, and 0.9 ml of the anatase-type titanium oxide sol prepared above was added thereto, followed by stirring for mixing. The solution was transferred to a hydrothermal reaction vessel (HU-50, manufactured by SAN-AI Science Co. Ltd.), and a reaction was allowed to proceed at 150° C. for 5 hr. After the completion of the reaction, the reaction vessel was cooled to a temperature of 50° C. or below. DMF was removed by an evaporator, and 10 ml of distilled water was added to the residue to prepare an aqueous polyethylene glycol-bonded titanium oxide solution. The aqueous polyethylene glycol-bonded titanium oxide solution was subjected to HPLC under the following conditions. As a result, an UV absorption peak was observed in a fraction passed through the column, and this fraction was recovered.

HPLC: AKTA purifier, manufactured by Amersham Biosciences

Column: HiPrep 16/60 Sephacryl S-300HR, manufactured by Amersham Biosciences

Mobile phase: phosphate buffer solution (pH 7.4)

Flow rate: 0.3 ml/min

This dispersion liquid was diluted with distilled water to prepare a 0.01% aqueous solution, and the dispersed particle diameter and zeta potential were determined by a dynamic light scattering method and were found to be 45.4 nm and 1.1 mV, respectively. This measurement was carried out with Zetasizer Nano ZS by charging 0.75 ml of the aqueous polyethylene glycol-bonded titanium oxide solution into a zeta potential measuring cell, setting various parameters of the solvent to the same values as water, and conducting the measurement at 25° C.

Example 4

Cell Killing Test by Ultrasonic Irradiation

At the outset, the following semiconductor particles were provided.

$TiO_2$/PAA particles (prepared in Example 1)

$SnO_2$ particles (manufactured by C.I. KASEI CO., LTD., SNW 15 wt %-G02, neutral dispersion, dispersed particle diameter 39 nm)

ZnO particles (manufactured by C.I. KASEI CO., LTD., Zn MS 15 wt %-G01, neutral dispersion, dispersed particle diameter 67 nm)

CdSe particles (manufactured by Quantum Dot, Qdot655 labeled with protein A, neutral dispersion, dispersed particle diameter 8 nm)

The dispersed particle diameters of the above-described various particles were determined by the dynamic light scattering method described in Example 1.

Next, the semiconductor particles were dispersed in a PBS buffer solution (pH 6.8). This dispersion liquid was added to a 10% serum-added RPMI 1640 medium (manufactured by Invitrogen) containing $1\times10^4$ cells/ml Jurkat cells at a ratio of 1:10 to a final concentration of 0.05% to prepare a test solution.

For comparison, particles which are not the following metal semiconductor particles were provided and were used for the preparation of a test solution in the same manner as described above.

$SiO_2$ particles (manufactured by C.I. KASEI CO., LTD., Si MS 10 wt %-G360, neutral dispersion, dispersed particle diameter 105 nm)

Au particles (manufactured by ICN Biomedicals, Inc., ProteinA 20 nm, Gold conjugate, neutral dispersion, dispersed particle diameter 40 nm)

The dispersed particle diameters of the above-described various particles were determined by the dynamic light scattering method described in Example 1.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm² and 50% duty cycle for one min to conduct a cell killing test. The results were as shown in FIG. 1. As shown in FIG. 1, all the semiconductor particle-added solutions had a low cell survival rate, that is, had a high kill rate, confirming that cells could be killed by ultrasonic irradiation. On the other hand, no cell killing effect was confirmed on $SiO_2$ particles and Au particles used for comparison.

Example 5

Dependency on Semiconductor Particle Concentration

A test on the dependency of cell killing by ultrasonic irradiation on semiconductor particle concentration was carried out using $TiO_2$ particles ($TiO_2$/PAA) prepared in Example 1. Titanium oxide particles were added to a PBS buffer solution (pH 6.8), and the dispersion liquid was added to a 100/0 serum-added RPMI 1640 medium (manufactured by Invitrogen) containing $1\times10^4$ cells/ml Jurkat cells at a ratio of 1:10 to final concentrations of 0.0010%, 0.01%, 0.05% and 0.1% to prepare test solutions. The test solutions were exposed to ultrasonic waves from an ultrasonic irradiation apparatus (ULTRASONIC APPARATUS ES-2: 1 MHz, manufactured by OG GIKEN CO., LTD.) under conditions of 0.5 W/cm² and 50% duty cycle for one min to conduct a cell killing test for studying the dependency of cell killing upon semiconductor particle concentration. The results were as shown in FIG. 2. As shown in FIG. 2, it was confirmed that the survival rate of the cells was lowered for all the concentrations of the titanium oxide particle-added solutions. In particular, the cell survival rate was lowered in the 0.05% (final concentration) solution, confirming that the final concentration which provided a high cell killing effect was 0.050%.

Example 6

Evaluation of Ability of Producing Superoxide Anion Upon Ultrasonic Irradiation

At the outset, the following semiconductor particles were provided.

$TiO_2$ particles (A) (manufactured by Ishihara Sangyo Kaisha Ltd., anatase-type titanium oxide, STS-240, neutral dispersion, dispersed particle diameter 52 nm)

$SnO_2$ particles (manufactured by C.I. KASEI CO., LTD., SNW 15 wt %-G02, neutral dispersion, dispersed particle diameter 39 nm)

ZnO particles (manufactured by C.I. KASEI CO., LTD., Zn MS 15 wt %-G01, neutral dispersion, dispersed particle diameter 67 nm)

Next, the semiconductor particles were dispersed in a PBS buffer solution (pH 6.8) to prepare a dispersion liquid having a final solid content of 0.1%. A reductive chromogenic reagent WST-1 (manufactured by DOJINDO LABORATORIES), which is a superoxide anion producing reagent, was added to the aqueous solution to give a concentration of 0.50%. Thus, a test solution was prepared.

For comparison, $SiO_2$ particles (manufactured by C.I. KASEI CO., LTD., Si MS 10 wt %-G360, neutral dispersion, dispersed particle diameter 105 nm) were provided as particles, which are not metal semiconductor particles, and were used for the preparation of a test solution in the same manner as described above.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm² and 50% duty cycle for 5 min, and the absorption at a wavelength of 450 nm was measured with an ultraviolet-visible spectrophotometer. The results were as shown in FIG. 3. As shown in FIG. 3, in all the particles which are semiconductor particles, an increase in absorbance was observed as a result of the production of yellow formazan upon the decomposition of WST-1. That is, it was confirmed that $TiO_2$ particles, $SnO_2$ particles and ZnO particles produce a superoxide anion upon ultrasonic irradiation.

Example 7

Evaluation of Ability of Producing Hydroxyradicals Upon Ultrasonic Irradiation

At the outset, the following semiconductor particles were provided.

$TiO_2$ particles (A) (manufactured by Ishihara Sangyo Kaisha Ltd., anatase-type titanium oxide, STS-240, neutral dispersion, dispersed particle diameter 52 nm)

$SnO_2$ particles (manufactured by C.I. KASEI CO., LTD., SNW 15 wt %-G02, neutral dispersion, dispersed particle diameter 39 nm)

ZnO particles (manufactured by C.I. KASEI CO., LTD., Zn MS 15 wt %-G01, neutral dispersion, dispersed particle diameter 67 nm)

Next, the semiconductor particles were added to a PBS buffer solution (pH 6.8) to prepare a dispersion liquid having a final solid content of 0.1%. Hydroxyphenylfluorescein as a fluorescence reagent for active oxygen detection (HPF, manufactured by Daiichi Pure Chemicals Co., Ltd.) was added as a hydroxy radical generating reagent to the metal oxide particle-containing solution so that the concentration of the reagent was brought to 5 μM. Thus, a test solution was prepared.

For comparison, $SiO_2$ particles (manufactured by C.I. KASEI CO., LTD., Si MS 10 wt %-G360, neutral dispersion, dispersed particle diameter 105 nm) were provided and were used for the preparation of a test solution in the same manner as described above.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm² and 50% duty cycle for 5 min, and the fluorescence intensity at a wavelength of Ex=490 nm and Em=515 nm was measured with a fluorophotometer. The results were as shown in FIG. 4. As shown in FIG. 4, in all the particles which are semiconductor particles, an increase in fluorescence intensity was observed as a result of HPF reaction to produce fluorescein. That is, it was confirmed that $TiO_2$ particles, $SnO_2$ particles and ZnO particles produce hydroxy radicals upon ultrasonic irradiation.

Example 8

Evaluation of Ability of Producing Hydrogen Peroxide Upon Ultrasonic Irradiation At the outset, the following semiconductor particles were provided.

$TiO_2$ particles (A) (manufactured by Ishihara Sangyo Kaisha Ltd., anatase-type titanium oxide, STS-240, neutral dispersion, dispersed particle diameter 52 nm)

$SnO_2$ particles (manufactured by C.I. KASEI CO., LTD., SNW 15 wt %-G02, neutral dispersion, dispersed particle diameter 39 nm)

ZnO particles (manufactured by C.I. KASEI CO., LTD., Zn MS 15 wt %-G01, neutral dispersion, dispersed particle diameter 67 nm)

Next, the semiconductor particles were added to a PBS buffer solution (pH 6.8) to prepare a dispersion liquid having a final solid content of 0.1%. Thus, a test solution was prepared.

For comparison, $SiO_2$ particles (manufactured by C.I. KASEI CO., LTD., Si MS 10 wt %-G360, neutral dispersion, dispersed particle diameter 105 nm) were provided and were used for the preparation of a test solution in the same manner as described above.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm² and 50% duty cycle for 5 min, and 100 μl of the solution was collected and was measured with an Amplex Red Hydrogen Peroxide/Peroxidase Assay Kit (manufactured by Molecular Probes) according to the instruction manual of this kit. The results were as shown in FIG. 5. As shown in FIG. 5, it was confirmed that the $TiO_2$ particles could efficiently produce hydrogen peroxide upon ultrasonic irradiation.

Example 9

Evaluation of Ability of Producing Singlet Oxygen Upon Ultrasonic Irradiation

At the outset, the following semiconductor particles were provided.

$TiO_2$ particles (A) (manufactured by Ishihara Sangyo Kaisha Ltd., anatase-type titanium oxide, STS-240, neutral dispersion, dispersed particle diameter 52 nm)

$SnO_2$ particles (manufactured by C.I. KASEI CO., LTD., SNW 15 wt %-G02, neutral dispersion, dispersed particle diameter 39 nm)

ZnO particles (manufactured by C.I. KASEI CO., LTD., Zn MS 15 wt %-G01, neutral dispersion, dispersed particle diameter 67 nm)

$TiO_2$/PAA (prepared in Example 1)
$TiO_2$/PEG (prepared in Example 3)

Next, the semiconductor particles were added to a PBS buffer solution (pH 6.8) to prepare a dispersion liquid having a final solid content of 0.05%. Thus, a test solution was prepared.

For comparison, $SiO_2$ particles (manufactured by C.I. KASEI CO., LTD., Si MS 10 wt %-G360, neutral dispersion, dispersed particle diameter 105 nm) were provided and were used for the preparation of a test solution in the same manner as described above.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm² and 50% duty cycle for 5 min, and 100 μl of the solution was collected, followed by the measurement of fluorescence intensity at Ex=488 nm and Em=525 nm attributable to singlet oxygen with a fluorophotometer according to an instruction manual of Singlet Oxygen Sensor Green Reagent (Molecular Probes) using the kit of Molecular Probes. The results were as shown in FIG. 6. As shown in FIG. 6, it was confirmed that the $TiO_2$ particles could efficiently produce singlet oxygen upon ultrasonic irradiation.

Example 10

Dependency on Frequency

In a 2-ml microtube, a solution having a composition comprising PBS buffer solution: 850 μl, a reductive chromogenic reagent WST-1 (manufactured by DOJINDO LABORATORIES): 50 µl, and 0.1% titanium oxide particles: 100 µl was prepared. $TiO_2$ particles (A) (manufactured by Ishihara Sangyo Kaisha Ltd., anatase-type titanium oxide, STS-240, neutral dispersion, dispersed particle diameter 52 nm) were used as the titanium oxide particles.

The microtube thus obtained was irradiated with ultrasonic waves at the same intensity in a water bath at a distance of 3 cm from an ultrasonic vibrator with a multi-frequency ultrasonic wave generator (MODEL 4021 {KAIJYO}, output: 200 W). Sampling was carried out by 200 µl upon the elapse of each of 0 (zero) min, 3 min and 6 min each after the ultrasonic irradiation, followed by the measurement of superoxide anion by the same method as in Example 6. The measurement was carried out for each irradiation frequency at each of 28, 50, 100, 200, and 600 kHz. Further, the same measurement was also carried out for the case where the titanium oxide particles were not added (control). The results were as shown in FIG. 7. As shown in FIG. 7, the superoxide anion was produced in the presence of titanium, and the results were significant at the highest irradiation frequency 600 kHz.

Example 11

Stability of Particles

The following particles were dispersed to a final concentration of 0.01% to each of water, a PBS buffer solution (pH 7.4), and a 10% serum-containing RPMI 1640 medium to prepare samples.

Titanium oxide (C) (a liquid of P25 particles, manufactured by Nippon Aerosil Co., Ltd., dispersed in a PBS buffer solution (pH 6.8), dispersed particle diameter 500 nm)

$TiO_2$/PAA particles prepared in Example 1

$TiO_2$/PEG particles prepared in Example 3

Titanium oxide (A) (STS 240, manufactured by Ishihara Sangyo Kaisha Ltd., neutral dispersion, dispersed particle diameter 52 nm)

Titanium oxide (B) (TKS-203, manufactured by Tayca Corporation, anatase-type titanium oxide, neutral dispersion, dispersed particle diameter 120 nm)

$SnO_2$ particles (manufactured by C.I. KASEI CO., LTD., SNW 15 wt %-G02, neutral dispersion, dispersed particle diameter 39 nm)

ZnO particles (manufactured by C.I. KASEI CO., LTD., Zn MS 15 wt %-G01, neutral dispersion, dispersed particle diameter 67 nm)

A change in average dispersed particle diameter in each dispersion liquid was measured as an index for the stability of each particle. This measurement was carried out by a dynamic light scattering method with Zetasizer Nano ZS (manufactured by SYSMEX CORPORATION) by charging 0.1 ml of the dispersion liquid in a quartz measurement cell, setting various parameters of the solvent to the same values as in water, and measuring the average dispersed particle diameter at 25° C. after the elapse of 1 hr and 24 hr. For each dispersion liquid, the measured average dispersed particle diameter is shown in Table 1. As shown in Table 1, as compared with titanium oxide (A) and titanium oxide (B) commercially available as a neutral dispersion, $TiO_2$/PAA and $TiO_2$/PEG prepared in this Example had no significant change in average dispersed particle diameter and thus had excellent stability.

TABLE 1

|  | $H_2O$ | | PBS | | Medium | |
| --- | --- | --- | --- | --- | --- | --- |
|  | 1 hr | 24 hr | 1 hr | 24 hr | 1 hr | 24 hr |
| $TiO_2$ (C) | 871 | 522 | 2720 | 1030 | 1170 | 588 |
| $TiO_2$/PAA | 66.5 | 57.2 | 59.6 | 53.7 | 57.3 | 53.2 |
| $TiO_2$/PEG | 47.2 | 47.3 | 43.2 | 59.3 | 50.5 | 78.1 |
| $TiO_2$ (A) | 52 | 47.5 | 47.4 | 164 | 58.1 | 137 |
| $TiO_2$ (B) | 127 | 122 | 134 | 152 | 676 | 665 |
| $SnO_2$ | 42.3 | 43.1 | 35.2 | 40.2 | 144 | 393 |
| ZnO | 66.9 | 65.3 | 76 | 84.8 | 122 | 135 |

(unit: nm)

Example 12

Cell Killing Test by Ultrasonic Irradiation

At the outset, $TiO_2$/PAA particles (prepared in Example 1, neutral dispersion, dispersed particle diameter 45.5 nm) were dispersed in a PBS buffer solution (pH 6.8). This dispersion liquid was added to a 10% serum-added RPMI 1640 medium (manufactured by Invitrogen) containing $1 \times 10^4$ cells/ml Jurkat cells at a ratio of 1:10 to a final $TiO_2$/PAA particle concentration of 0.01% and 0.001% to prepare test solutions.

For comparison, $TiO_2$ particles (C) (a liquid of P25 particles (manufactured by Nippon Aerosil Co., Ltd.) dispersed in a PBS buffer solution (pH 6.8), dispersed particle diameter 500 nm) were provided and were used for the preparation of test solutions in the same manner as described above. The dispersed particle diameter of the above various particles was measured by the dynamic light scattering method described in Example 1.

Each of the test solutions thus obtained was irradiated with ultrasonic waves for one min with an ultrasonic irradiation apparatus (ULTRASONIC APPARATUS ES-2: 1 MHz, manufactured by OG GIKEN CO., LTD.) under conditions of 0.5 W/cm² and 50% duty cycle to conduct a cell killing test. The results were as shown in FIG. 8. As shown in FIG. 8, it was confirmed that all the solutions to which $TiO_2$/PAA particles having a dispersed particle diameter of 45.5 nm were added, had a high tumor cell killing effect. On the other hand, no cell killing effect was confirmed on $TiO_2$ particles (C) having a dispersed particle diameter of 500 nm used for comparison.

Example 13

Evaluation of Ability of Producing Hydroxy Radicals Upon Ultrasonic Irradiation

At the outset, the following semiconductor particles were provided.

$TiO_2$ particles (A) (manufactured by Ishihara Sangyo Kaisha Ltd., anatase-type titanium oxide, STS-240, neutral dispersion, dispersed particle diameter 52 nm)

$TiO_2$ particles (D) (manufactured by Ishihara Sangyo Kaisha Ltd., anatase-type titanium oxide, STS-230, neutral dispersion, dispersed particle diameter 15 nm)

$TiO_2$ particles (C) (a liquid of P25 particles (manufactured by Nippon Aerosil Co., Ltd.) dispersed in a PBS buffer solution (pH 6.8), dispersed particle diameter 500 nm)

Next, the semiconductor particles were added to a PBS buffer solution (pH 6.8) to prepare a dispersion liquid having a final solid concentration of 0.05%. Hydroxyphenylfluorescein as a fluorescence reagent for active oxygen detection (HPF, manufactured by Daiichi Pure Chemicals Co., Ltd.)

was added as a hydroxy radical generating reagent to the metal oxide particle-containing solution so that the concentration of the reagent was brought to 5 (M. Thus, a test solution was prepared.

Further, a PBS buffer solution (pH 6.8) was provided as control, and test solutions were prepared in the same manner as described above.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm2 and 50% duty cycle for 5 min, and the fluorescence intensity at a wavelength of Ex=490 nm and Em=515 nm attributable to hydroxy radicals was measured with a fluorophotometer. The results were as shown in FIG. 9. As shown in FIG. 9, it was confirmed that, in TiO2 particles (A) having a dispersed particle diameter of 52 nm and TiO2 particles (D) having a dispersed particle diameter of 15 nm, hydroxy radical production was observed more significantly than the control. On the other hand, for TiO2 particles (C) having a dispersed particle diameter of 500 nm, any hydroxy radical production was not confirmed.

Example 14

Safety of Particles

At the outset, TiO2/PAA particles (prepared in Example 1, neutral dispersion, dispersed particle diameter 45.5 nm), TiO2/PEI particles (prepared in Example 2, neutral dispersion, dispersed particle diameter 67.7 nm), and TiO2/PEG particles (prepared in Example 3, neutral dispersion, dispersed particle diameter 45.4 nm) were dispersed in a PBS buffer solution (pH 6.8) to prepare various dispersion liquids. Each of these dispersion liquids was added at a ratio of 1:10 to a 10%/o serum-added RPMI 1640 medium (manufactured by Invitrogen) containing 1 (104 cells/ml Jurkat cells to final TiO2-based composite particle concentrations of 0.1, 0.01 and 0.001% by weight to prepare test solutions. Separately, for a control experiment, only the PBS buffer solution was added in the same manner as described above to prepare a control test solution. After the preparation, the solutions were cultured in a $CO_2$ incubator at 37° C. for 24 hr, and the viable cell count was determined with CellTiterGro Kit (manufactured by Bio-Rad). The results of comparison of the test solutions by presuming the survival rate of the control test solution to be 100% are shown in FIG. 10. As shown in FIG. 10, for all the test solutions respectively having final TiO2-based composite particle concentrations of 0.1, 0.01 and 0.001% by weight, a high cell survival rate, that is, a high level of safety could be realized.

Example 15

Test on Cell Killing Upon Ultrasonic Irradiation Using Polymer-Bonded TiO2 Particles TiO2/PAA particles (prepared in Example 1), TiO2/PEI particles (prepared in Example 2) and TiO2/PEG particles (prepared in Example 3) were dispersed in a PBS buffer solution (pH 6.8). This dispersion liquid was added to a 10% serum-added RPMI 1640 medium (manufactured by Invitrogen) containing 1 (104 cells/ml Jurkat cells at a ratio of 1:10 to a final concentration of 0.05% to prepare a test solution.

Each of the test solutions thus obtained was exposed to ultrasonic waves from an ultrasonic irradiation apparatus (ULTRASONIC APPARATUS ES-2: 1 MHz, manufactured by OG GIKEN CO., LTD.) under conditions of 0.5 W/cm$^2$ and 50% duty cycle for one min to conduct a cell killing test. The results were as shown in FIG. 11. As shown in FIG. 11, all the solutions to which TiO$_2$/PAA particles, TiO$_2$/PEI particles and TiO$_2$/PEG particles had been added, had a low cell survival rate, that is, had a high kill rate. In particular, it was confirmed that the solution to which TiO$_2$/PEG particles had been added, had a very low cell survival rate, confirming that the TiO$_2$/PEG particles had a particularly high effect of killing cells upon ultrasonic irradiation.

Example 16

Test 2 on Cell Killing Upon Ultrasonic Irradiation

At the outset, TiO$_2$/PAA particles (prepared in Example 1, neutral dispersion, dispersed particle diameter 45.5 nm) were dispersed in a PBS buffer solution (pH 6.8). This dispersion liquid was added to a 10% serum-added RPMI 1640 medium (manufactured by Invitrogen) containing $5 \times 10^4$ cells/ml Jurkat cells at a ratio of 1:10 to a final TiO$_2$/PAA particle concentration of 0.05% to prepare 3 ml of a test solution.

Further, a PBS buffer solution (pH 6.8) was provided as control, and test solutions were prepared in the same manner as described above.

Each of the test solutions was continuously irradiated with ultrasonic waves using an ultrasonic irradiation apparatus (EH2435: 5 MHz, manufactured by Matsushita Electric Works, Ltd.) at the maximum output for 2 min to conduct a cell killing test. The results were as shown in FIG. 12. The survival rate was determined by presuming the number of viable cells in a sample added with PBS buffer solution but not irradiated with ultrasonic waves to be 100%. As shown in FIG. 12, the solution to which TiO$_2$/PAA particles having a dispersed particle diameter of 45.5 nm had been added, had a high tumor cell killing effect.

Example 17

Antitumor Effect Test

A human bladder cancer-derived established cell line (T-24) was subcutaneously inoculated into nude mice (Balb/c, male, 3 weeks old) to form a tumor having a size of about 0.63 mm$^3$. PAA-TiO$_2$ prepared in Example 1 was diluted with a PBS buffer solution to 0.5%, and 100 µl of the diluted solution was topically injected into the tumor. Ultrasonic waves of 1 MHz were applied, 24 hr after the administration, under conditions of time one min, output 1 W, and pulse 50% with an ultrasonic wave irradiation apparatus (ULTRASONIC APPARATUS ES-2: 1 MHz, manufactured by OG GIKEN CO., LTD.; probe diameter 10 mm). A water soluble polymer gel was coated onto the skin, and a probe (an ultrasonic irradiation part) was brought into intimate contact with the coating followed by the ultrasonic irradiation. One group consisted of 6 mice, and a control group consisted of mice, to which only PBS had been administered, or untreated mice. After the ultrasonic irradiation, the tumor volume of each individual was measured, and the tumor volume (relative tumor growth rate) at each measuring point was determined by presuming the tumor volume, before PAA-TiO$_2$ administration at the ultrasonic irradiation date (day 0) for each individual, to be 1.

The results are shown in FIG. 13.

As shown in FIG. 13, a significant growth inhibitory effect of the tumor was observed only when the adoption of titanium oxide+ultrasonic irradiation was satisfied.

The invention claimed is:

1. A method for treating cancer, characterized by administering a cell killer to an animal including human, and exposing cancer cells to ultrasonic waves of 400 KHz to 20 MHz after the administration to convert the cell killer to a cytotoxin, whereby the cytotoxin kills the cancer cells,
wherein the cell killer comprises metal semiconductor particles and is convertible to the cytotoxin upon irradiation of ultrasonic waves of 400 KHz to 20 MHz, and the metal semiconductor particles comprise a metal oxide having a particle diameter of 20-200 nm, and
wherein the semiconductor particles are bonded to polyethylene glycol on a surface of the particles.

2. The method according to claim 1, wherein the cytotoxin is produced by radical species which are produced by the semiconductor particles upon ultrasonic irradiation of ultrasonic waves of 400 KHz to 20 MHz.

3. The method according to claim 1, wherein the metal semiconductor particles comprise at least one of semiconductor particles selected from the group consisting of TiO2, SnO2, and ZnO.

4. The method according to claim 3, wherein the semiconductor particles are made of TiO2.

5. The method according to claim 1, wherein the semiconductor particles are dispersed in a solvent to be in the form of dispersion.

6. The method according to claim 5, wherein the solvent has neutral pH.

7. The method according to claim 5, wherein the solvent is physiological saline.

8. The method according to claim 5, wherein a content of the semiconductor particles in the dispersion is 0.001 to 1% by weight.

9. The method according to claim 1, wherein the semiconductor particles are in the form of a lyophilized powder.

10. The method according to claim 1, wherein the cell killer is administered into a body through an intravenous administration route.

11. The method according to claim 1, wherein the cell killer is administered into a body through a subcutaneous administration route.

12. The method according to claim 1, wherein when the metal semiconductor particles are exposed to irradiation of ultrasonic waves of 400 KHz to 20 MHz they generate cytotoxin in the form of super oxide anion and singlet oxygen.

13. The method according to claim 1, wherein the cell killer is systemically administered into a body.

14. The method according to claim 1, wherein the semiconductor particles are directly bonded to polyethylene glycol on a surface of the particles.

15. The method according to claim 1, wherein no component containing a lipophilic group is bonded on the surface of the particles.

* * * * *